United States Patent
Fischell et al.

(10) Patent No.: US 6,350,226 B1
(45) Date of Patent: Feb. 26, 2002

(54) RADIOISOTOPE BANDAGE FOR REDUCING SCAR TISSUE FORMATION

(75) Inventors: Robert E. Fischell, Dayton, MD (US); David R. Fischell, Fair Haven, NJ (US)

(73) Assignee: Cathco, Inc., Dayton, MD (US)

( * ) Notice: Subject to any disclaimer, the term of this patent is extended or adjusted under 35 U.S.C. 154(b) by 0 days.

(21) Appl. No.: 09/637,999

(22) Filed: Aug. 15, 2000

(51) Int. Cl.⁷ .................................................. A61N 5/00
(52) U.S. Cl. .......................................................... 600/1
(58) Field of Search ................................ 600/1, 2, 3, 4, 600/5, 6, 7, 8; 604/368, 358, 375

(56) References Cited

U.S. PATENT DOCUMENTS

| | | | | |
|---|---|---|---|---|
| 4,215,693 A | * | 8/1980 | Rotham et al. | 604/368 |
| 4,946,435 A | * | 8/1990 | Suthanthiran et al. | 600/3 |
| 5,871,708 A | * | 2/1999 | Park et al. | 600/1 |

* cited by examiner

Primary Examiner—Kevin Shaver
Assistant Examiner—Brian Szmal

(57) ABSTRACT

Disclosed is a novel wound dressing which applies ionizing radiation to the surface of the wound as soon after the wound is created as is possible. Optimally, the radiation has a range which extends to the bottom surface of the skin but not significantly beyond that depth. An example of a radioactive source that can apply this type of radiation dosing is a beta particle emitting radioisotope such as phosphorous-32 which has a range of approximately 3.5 mm for 90% of the electrons that it emits. Even very small amounts of phosphorous-32 can provide a sufficiently high level of irradiation to significantly diminish scar tissue formation. The radioactive bandage would typically be an elongated flexible structure which can be applied along a wound or surgical incision. Typically, the radioactive bandage would extend for approximately 1 to 5 mm beyond the cut in all directions. The radioactive bandage would include a shield structure which surrounds the thin, elongated radioactive portion thus disallowing stray radiation outward from the patient's skin. A radiation dose applied to the top of the incision of between 500 and 2000 cGy can substantially reduce scar tissue formation for most patients.

11 Claims, 2 Drawing Sheets

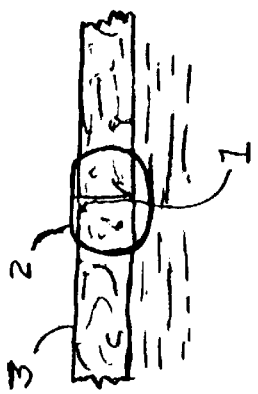
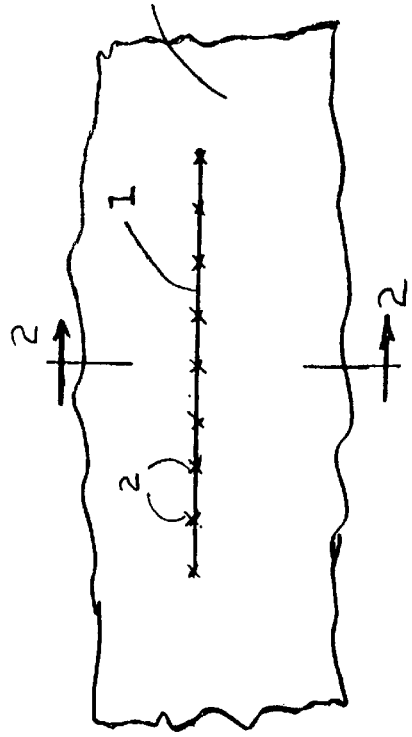
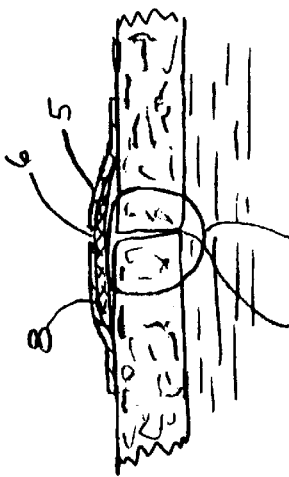
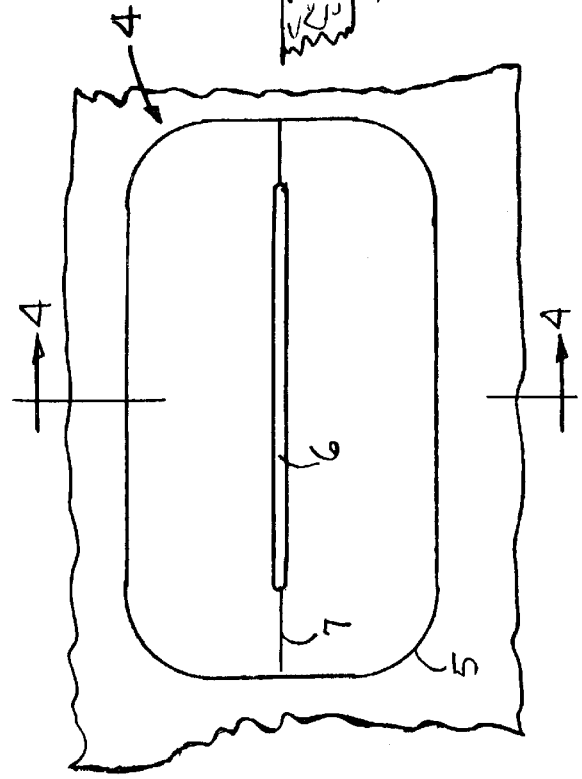

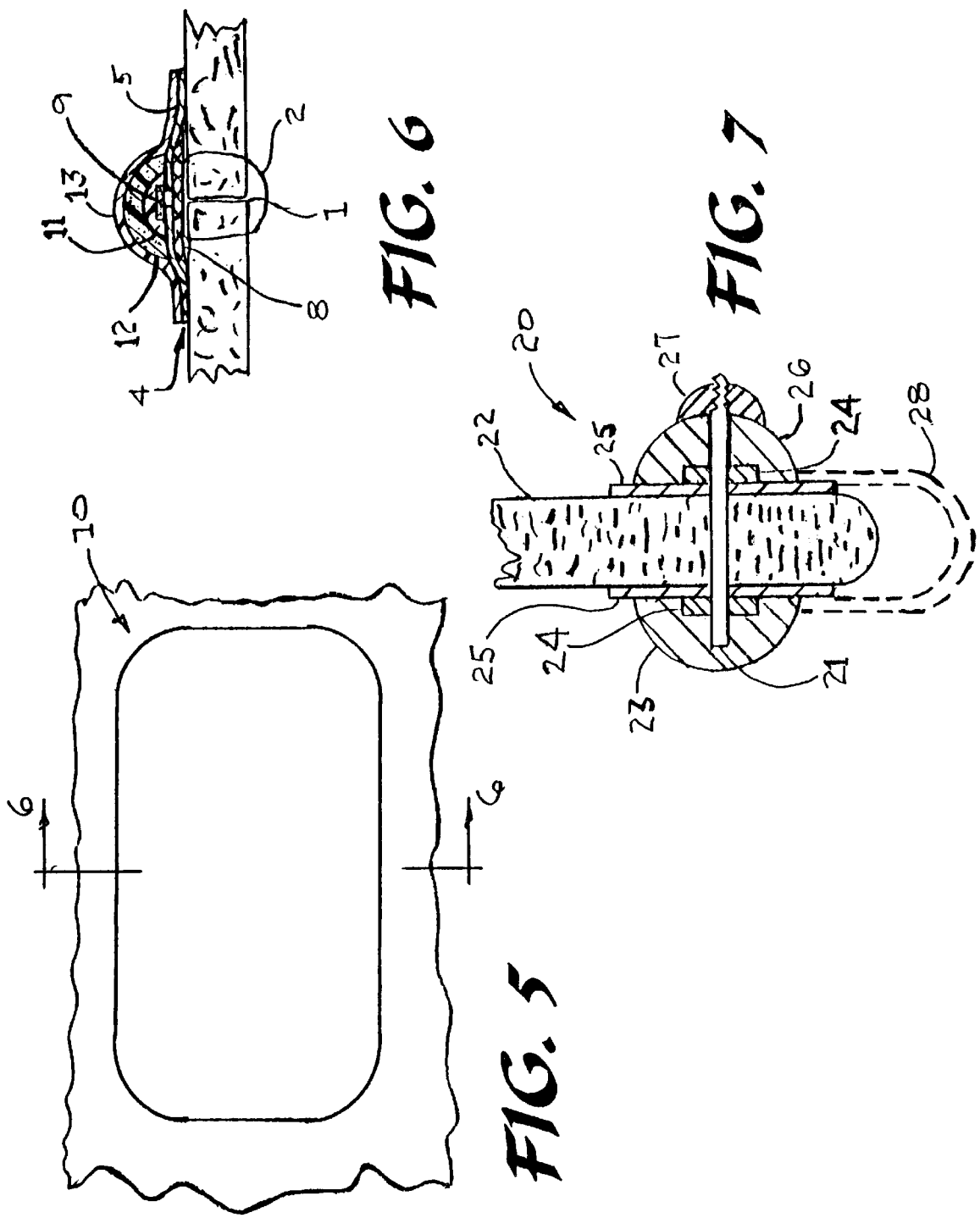

RADIOISOTOPE BANDAGE FOR REDUCING SCAR TISSUE FORMATION

FIELD OF USE

This invention is in the field of medical devices that prevent the formation of scar tissue. Specifically, this invention is a radioactive bandage to be applied to wounds to reduce the level of scar tissue formation on the skin surface.

BACKGROUND OF THE INVENTION

When an incision is made in the skin either accidentally or as part of a surgical procedure, the body produces scar tissue to help close the wound. A sterile wound dressing assists in eliminating an infection, however, the wound dressing has no significant effect in reducing the extent of scar tissue formation. Although some patients may have a minimum production of scar tissue, other patients can produce a level of scar tissue which is to some extent disfiguring. An extreme example of excessive scar tissue formation is the case of keloids. A well known treatment for keloids is surgical excision of the excessive scar tissue followed by several sessions of fractionated radiation typically using x-rays. This procedure, though successful in approximately 75% of all cases, is considerably expensive and time consuming.

SUMMARY OF THE INVENTION

The present invention is a unique wound dressing which applies ionizing radiation to the surface of the wound as soon after the wound is created as is possible. Optimally, the radiation has a range which extends to the bottom surface of the skin but not significantly beyond that depth. An example of a radioactive source that can apply this type of radiation dosing is a beta particle emitting radioisotope such as phosphorous-32 which has a range of approximately 3.5 mm for 90% of the electrons that it emits. Furthermore, phosphorous-32 has a half-life of 14.3 days which means that it has a very high rate of specific activity. Therefore, even very small amounts of phosphorous-32 can provide a sufficiently high level of irradiation to significantly diminish scar tissue formation.

The radioactive bandage for cuts in the skin would typically be an elongated, substantially one-dimensional, flexible structure which can be applied along a wound or surgical incision. Typically, the radioactive bandage would extend for approximately 1 to 5 mm beyond the cut in all directions. The radioactive bandage would include a shield structure which surrounds the thin, elongated radioactive portion thus disallowing stray radiation outward from the patient's skin. Specialized shapes for the radioactive bandage could be employed. For example, a hemispherical shaped radioactive bandage could be applied on an earlobe at the site where the lobe was pierced to disallow a keloid formation at that site.

To treat a wound with the present invention, one could first place a sterile bandage over the wound. Typically, such a sterile bandage would have a piece of sterile gauze extending for approximately 5mm beyond the extremities of the wound. The sterile bandage would also include an adhesive tape to hold the sterile gauze in place. The radioactive bandage would then be placed over such a bandage to apply a prescribed dose of radiation to the wound site.

Thus it is an object of this invention to reduce the formation of scar tissue for incisions into the skin which occur either accidentally or as part of a surgical procedure by means of a radioactive bandage that applies a prescribed dose of radiation to the wound site.

Another object of this invention is to utilize a radioactive bandage which has an elongated, substantially one-dimensional, structure which lies generally along the incision where it is desired to reduce the formation of scar tissue.

Still another object of this invention is to utilize a beta particle emitting radioisotope as the source of radiation for the radioactive bandage.

Still another object of this invention is to first place a sterile wound dressing on the skin incision and then place a radioactive bandage over that dressing.

Still another object of this invention is to provide a shielding means along the radioactive bandage to essentially eliminate exposure to ionizing radiation except as desired at the site of the wound.

Still another object of this invention is to have a shape of the radioactive bandage which is dictated by the shape and extent of the incision into the skin.

These and other objects and advantages of this invention will become obvious to a person of ordinary skill in this art upon reading of the detailed description of this invention including the associated drawings as presented herein.

BRIEF DESCRIPTION OF THE DRAWINGS

FIG. 1 is a top view of a straight line skin incision which is closed with sutures.

FIG. 2 is a cross section of the skin incision at section 2—2 of FIG. 1.

FIG. 3 is a top view of a sterile dressing placed upon the incision that was shown in FIG. 1.

FIG. 4 is a cross section of the incision and the sterile dressing shown at section 4—4 of FIG. 3.

FIG. 5 is a top view of a radioactive bandage applied on top of the dressing shown in FIG. 3.

FIG. 6 is a cross section of the wound at section 6—6 of FIG. 5 showing the cross section of the sterile dressing and the radioactive bandage.

FIG. 7 is a cross section of a radioisotope bandage designed specifically for preventing scar tissue formation in the ear lobe of a human subject.

DETAILED DESCRIPTION OF THE DRAWINGS

FIG. 1 is a top view of a cut or incision 1 in the skin 3, which incision is closed by means of sutures 2.

FIG. 2 is a cross section of the skin 3 showing a suture 2 which is used to hold together the incision 1 while the cut is healing. The technique of using sutures 2 to close incisions 1 is, of course, very well known as a part of any surgical procedure. It should also be understood that the incision 1 could have been made inadvertently by means of a razor or knife or any other sharp object.

FIGS. 3 and 4 show a sterile dressing 4 applied to the incision 1 and over the sutures 2. The sterile dressing 4 has a gauze 8 placed under a pressure sensitive adhesive tape 5. The center of the bandage along the line of the incision 1 could typically have an open slot 6 and an extended center line 7 each of which mark the position of the incision 1. The reason for the open slot is so that the incision 1 can be seen through the gauze 8 so that the slot is placed exactly over the incision 1.

FIGS. 5 and 6 illustrate the significant details of the present invention. FIGS. 5 and 6 show the radioactive bandage 10 placed on top of the adhesive tape 5 of the sterile wound dressing 4 which has been placed on top of the sutures 2 and the incision 1. As seen in FIG. 5, the radioactive bandage 10 could extend completely over the dressing 4. Because the slot 6 provided the capability for the bandage 4 to be accurately placed over the incision 1, it follows that when the radioactive bandage 10 is accurately placed onto the bandage 4, the radioactive source 9 of the radioactive bandage 10 will also be accurately placed over the incision 1. As seen in FIGS. 5 and 6, the radioactive bandage 10 consists of an elongated, substantially one-dimensional, radioactive source 9 which contains the radioisotope which is the source of radiation that is used to provide a dose of ionizing radiation to at least the upper portions of the incision 1. Although the portions of the incision 1 closest to the radioisotope source 9 would encounter the highest dose of radiation, under most circumstances the entire incision 1 would be exposed to at least some level of radiation. The radioisotope source 9 might typically be an elastomer into which a radioisotope has been placed. A typical elastomer could be silicone rubber, polyurethane, polyethylene or any other similar material which could be made into an elongated source into which a radioisotope could be placed. A typical radioisotope would be the beta particle emitting isotope phosphorous-32. However, it should be understood that any isotope that produces either beta particles or low energy x-rays could be used for this purpose.

It is also seen in FIG. 6 that the radioactive bandage 10 has an elongated hemi-cylindrical radiation shield 11 which surrounds the source 9. The purpose of the shield 11 would be to absorb beta particles without the creation of a significant level of bremsstrahlung. Virtually any elastomer would serve that purpose. The hemi-cylindrical shield 12 shown in FIG. 6 would be a high density source which is placed to substantially reduce any stray radiation outward from the skin. The shield 12 might typically be formed from a high density metal such as tungsten impregnated into any one of several elastomers. The purpose of the shield 12 would be to absorb any photon emission caused by bremsstrahlung which resulted from a beta particle hitting the nucleus of some atom. If the radioactive source 9 was a low energy x-ray emitter, the radiation shields 11 and 12 might be combined into a single shield having a high density metal impregnated into some elastomer. The outer layer of the radioactive bandage 10 could be an adhesive tape 13 which is used to join the radioactive bandage 10 to the tape 5 of the sterile dressing 4.

Although FIG. 5 shows a generally elongated, rectangular structure it should be understood that the radioactive bandage could be made in any shape which best allows irradiation of the wound below. For example, in the case of a pierced earlobe which resulted in keloid formation, the radioisotope source 9 could be a cylindrical disk and the shielding could have a generally hemispherical shape.

A typical method for using the radioactive bandage 10 would be as follows:

(a) Place a sterile wound dressing over the site of a cut or a wound which is either caused by an accident or results from a surgical procedure, which cut or wound shall be referred to collectively as an incision.

(b) Place a radioactive bandage over the sterile wound dressing, the radioactive bandage including a radioisotope which is adapted to irradiate the incision in the skin.

An additional step in this method is to remove the radioactive bandage after a specific dose of radiation has been applied to the skin. Still another step in the method of use is to remove the radioactive bandage at a time when the wound dressing had to be changed. Still another method step is to remove the radioactive bandage when the sutures in the wound have to be removed.

The dose of radiation applied to the outer surface of the incision 1 can be adjusted by; (1) the source strength and type of radioisotope in the source 9; (2) by the combined thickness of the adhesive tape 5 and gauze bandage 8; and (3) the amount of time that the bandage 10 remains in place. Depending on the type of incision and the patient's propensity to produce scar tissue, the prescribed dose to the skin at the outer surface of the incision should be approximately in the range from 500 cGy to 2,000 cGy. It is well known in the art and science of radiation oncology to calculate from a known source strength of a particular isotope the dose that would be applied to the outer surface of the incision through the shielding of a gauze and/or adhesive tape in a specific period of time. For example, with a very thin gauze and tape so that there is a minimum of radiation shielding, a 2 cm long phosphorous-32 source having a source strength of 1.0 microCurie could apply a dose of 1,000±500 cGy in a time period of approximately 10 days. A time period of 7–10 days for the application of a radioisotope bandage of the type described herein would be near optimum. Fourteen days would be the maximum time period that a radioisotope bandage should remain in place on the skin.

FIG. 7 shows the specific embodiment of a radioisotope bandage for placement on a human ear lobe as would typically be used for the treatment of a keloid that sometimes occur after the ear lobe is pierced. Prior to placement of the ear lobe bandage 20 as shown in FIG. 7, surgical excision of the keloid would have taken place. The bandage 20 of FIG. 7 would then be applied to prevent the recurrence of the keloid. One embodiment of the bandage 20 consists of central pin 21 placed through the pierced ear lobe 22. On the left side of FIG. 7, is a radiation shield 23 that surrounds a radioisotope source 24 which is placed over sterile gauze 25. The shield 23 is fixedly attached to the pin 21 on one side of the ear lobe 22, but the shield 26 on the other side of the ear lobe 22 makes a sliding fit with the pin 21. The bandage 20 could be made with both of the shields 23 and 26 sliding onto the pin 21.

The radioisotope bandage 20 is assembled onto the ear lobe 22 by pre-assembling the pin 21 to the shield 23. The radioisotope sources 24 would then be placed in the cavities of the shield 23 and the shield 26. The sterile dressing 25 would then be placed through the central pin 21 and against the shield 23, or else the sterile dressing 25 could be placed (possibly with an adhesive tape) onto the ear lobe 22. The pin 21 would then be placed through the hole that was pierced in the ear lobe 22 and the second sterile dressing 25 would be placed on the other side of the ear. The shield 26, into which the radioisotope source 24 was placed, is then slid over the pin 21 and the nut 27 is screwed or otherwise detachably joined onto the pin 21 in a manner similar to an earring. The assembly of the bandage 20 would then be as shown in FIG. 7.

Also shown in FIG. 7 is an alternative holding means for holding the bandage 20 onto an ear lobe. Specifically, a deformable connector 28 (shown in dotted lines) that is fixedly attached to the radiation shields 23 and 26 could be used to secure the bandage onto the ear lobe 22. Another holding means (not shown) would be to use adhesive tape to secure the bandage 20 onto the ear lobe 22.

Although the drawings show that the radioactive bandage is placed over a wound dressing, it is clearly possible to have the radioactive bandage applied directly over the incision. To do this, one might use a sterile gauze that is placed on the underside of the radioactive bandage where it makes contact with the incision.

Various other modifications, adaptations, and alternative designs are of course possible in light of the above teachings. Therefore, it should be understood at this time that within the scope of the appended claims the invention may be practiced otherwise than as specifically described herein.

What is claimed is:

1. A radioactive bandage for placement over an incision in the skin of a human subject, the radioactive bandage having a radioisotope source formed into a substantially one-dimensional, elongated strip that is adapted to apply a prescribed dose of radiation in the approximate range between 500 cGy and 2,000 cGy to the outer surface of the skin along the incision in the human subject so as to diminish the formation of scar tissue at the site of the incision in that human subject; the radioactive bandage further comprising a sterile wound source is adapted to be placed over the incision, the radioisotope source being placed generally over the incision.

2. The radioactive bandage of claim 1 wherein the sterile wound dressing is adapted to include a locating means for accurately placing the radioisotope source over the incision.

3. A method to reduce the formation of scar tissue in an incision in the skin of a human subject, the method including the following steps:
   (a) placing a sterile wound dressing over the site of the incision in the skin of the human subject, the incision having an outer surface; and
   (b) placing a radioactive bandage having a radioisotope source over the sterile wound dressing, the radioisotope source being adapted to deliver a prescribed dose of radiation in the range of approximately 500 cGy and 2000 cGy to the outer surface of the incision in order to reduce the formation of scar tissue at the site of the incision in a time period of less than 14 days.

4. The method of claim 3 including the step of removing the radioactive bandage from the site of the incision after the prescribed dose of radiation has been applied to the incision.

5. The method of claim 3 including the step of removing the radioactive bandage at the time when the wound dressing is required to be changed.

6. The method of claim 3 including the step of placing sutures to close the incision prior to placing the sterile dressing over the incision, and the additional step of removing the radioactive bandage when the sutures are removed from the incision.

7. A device for decreasing scar tissue formation in the ear lobe of a human subject, the device comprising:
   radioisotope sources adapted to be placed on each side of the ear lobe, the radioisotope sources being adapted to provide a radiation dose to the outer skin surface on each side of the ear lobe between the two radioisotope sources that is approximately in the range between 500 cGy and 2,000 cGy;
   radiation shields on each side of the ear lobe that are adapted to decrease radiation exposure except to the ear lobe region between the two radioisotope sources; and
   holding means for holding the radiation sources and radiation shields onto each side of the ear lobe; and
   a sterile gauze dressing placed onto each side of the ear lobe between the ear lobe's skin and the radioisotope sources.

8. The device of claim 7 wherein the radioisotope source is phosphorous-32 having a source strength between 1 and 1,000 microCuries.

9. The device of claim 7 wherein the holding means is a central pin adapted to be placed through the ear lobe where it has been pierced, the central pin extending for a distance outward from each side of the ear lobe.

10. The device of claim 9 wherein the central pin is fixedly attached to one of the radiation shields.

11. The device of claim 9 wherein at least one of the radiation shields has a through hole that allows it to slide over the central pin, the device also including at least one holding means for preventing the device from accidental removal from the ear lobe of the human subject.

* * * * *